(12) United States Patent
Sonoo

(10) Patent No.: US 10,172,975 B2
(45) Date of Patent: Jan. 8, 2019

(54) GEL-FORMING AGENT COMPRISING SULFA AGENT AND CHITOSAN AGENT AND HAVING POWDERED DOSAGE FORM

(71) Applicant: GREENEVER, Kitasaku-gun, Nagano (JP)

(72) Inventor: Yoshiko Sonoo, Kitasaku-gun (JP)

(73) Assignee: GREENEVER, Kitasaku-gun (JP)

( * ) Notice: Subject to any disclaimer, the term of this patent is extended or adjusted under 35 U.S.C. 154(b) by 17 days.

(21) Appl. No.: 15/107,850

(22) PCT Filed: Dec. 22, 2014

(86) PCT No.: PCT/JP2014/083954
§ 371 (c)(1),
(2) Date: Jun. 23, 2016

(87) PCT Pub. No.: WO2015/098864
PCT Pub. Date: Jul. 2, 2015

(65) Prior Publication Data
US 2016/0325012 A1    Nov. 10, 2016

(30) Foreign Application Priority Data
Dec. 24, 2013  (JP) .................................. 2013-265620

(51) Int. Cl.
| A61L 26/00 | (2006.01) |
| A61L 31/04 | (2006.01) |
| A61L 31/16 | (2006.01) |
| A61K 31/635 | (2006.01) |

(52) U.S. Cl.
CPC ........ *A61L 26/0066* (2013.01); *A61K 31/635* (2013.01); *A61L 26/0023* (2013.01); *A61L 26/0028* (2013.01); *A61L 31/042* (2013.01); *A61L 31/16* (2013.01); *A61L 2300/216* (2013.01); *A61L 2300/406* (2013.01)

(58) Field of Classification Search
CPC ............ A61L 26/0066; A61L 26/0028; A61L 26/0023; A61L 31/625; A61L 31/042; A61L 31/16; A61K 31/635
See application file for complete search history.

(56) References Cited

U.S. PATENT DOCUMENTS

| 2,386,157 | A | * | 10/1945 | Barthen et al. | ....... A61L 2/0088 |
| | | | | | 206/213.1 |
| 4,532,134 | A | * | 7/1985 | Malette | ................. A61K 31/715 |
| | | | | | 424/538 |
| 5,744,162 | A | * | 4/1998 | Okabe | ................... A61K 9/7061 |
| | | | | | 424/448 |
| 6,379,702 | B1 | | 4/2002 | Lorenz et al. | |
| 2010/0260809 | A1 | | 10/2010 | Valentova et al. | |
| 2010/0316715 | A1 | | 12/2010 | Andersson | |
| 2011/0319805 | A1 | | 12/2011 | Morris | |
| 2013/0029030 | A1 | * | 1/2013 | Larsen | .................. A61L 15/325 |
| | | | | | 427/2.31 |
| 2014/0274943 | A1 | | 9/2014 | Subramaniam et al. | |

FOREIGN PATENT DOCUMENTS

| CN | 1410072 A | 4/2003 | |
| EP | 0105106 A2 * | 4/1984 | ........... A61K 31/715 |
| EP | 2228078 A1 | 9/2010 | |
| GB | 2 327 344 A | 1/1999 | |
| JP | 4-139131 A | 5/1992 | |
| JP | 2003-62057 A | 3/2003 | |
| JP | 2004-501956 A | 1/2004 | |
| JP | 2010-540573 A | 12/2010 | |
| JP | 2011-500955 A | 1/2011 | |
| JP | 2012-523449 A | 10/2012 | |
| WO | WO 2010/119369 A2 | 10/2010 | |

OTHER PUBLICATIONS

Sandri et al., Carbohydrate Polymers, 2014, 102, p. 970-977, Available online Oct. 30, 2013. (Year: 2013).*
Biophilia, 2006, vol. 2, No. 1, pp. 20-26.
Chemical Education, 2001, vol. 49, No. 8, pp. 496-499.
International Search Report issued in PCT/JP2014/083954, dated Apr. 21, 2015.
Laura et al., "Characterization of silver sulfadiazine-loaded solid lipid nanoparticles by thermal analysis", J. Therm. Anal. Calorim., 2013, vol. 111, Issue 3, pp. 2149-2155.
Minami et al., "Application of Chitin and its Derivatives to Veterinary Medicine", Kachiku Shinryo, 2002, No. 474, pp. 757-767.

(Continued)

*Primary Examiner* — Jonathan S Lau
(74) *Attorney, Agent, or Firm* — Birch, Stewart, Kolasch & Birch, LLP

(57) ABSTRACT

The present invention relates to a gel-forming agent comprising a sulfa agent and a chitosan agent and having a powdered dosage form. In addition, the present invention provides a kit comprising the gel-forming agent of the present invention and a method comprising a step for applying the gel-forming agent of the present invention. According to the present invention, a gel-forming agent is provided that demonstrates a therapeutic effect that is more remarkable than that of conventional sulfa agents and chitosan agents alone, and more particularly, a gel-forming agent for protecting an exudative affected area and a gel-forming agent for treating a wound. Namely, by the applying the combination of a sulfa agent and a chitosan agent in the form of a powder, the pH of the affected area is maintained in a range that demonstrates a therapeutic effect, and antibacterial action of the sulfa agent is demonstrated. In addition, the moist environment at the affected area is suitably maintained for suitable granulation. In addition, as a result of being a powder, the use of a suitable dissipating container enables the gel-forming agent to be dispersed by a person performing treatment without making direct contact with the affected area.

12 Claims, 9 Drawing Sheets

(56) References Cited

OTHER PUBLICATIONS

Minami et al., "Biological Effect of Chitosan-Lactose Mixture and it's Clinical Application", Chitin and Chitosan Research, 2001, vol. 7, No. 3, pp. 268-272.
Okamoto et al., "Chitin/chitosan and wound healing", Journal of the Agricultural Chemical Society of Japan, 2004, vol. 78, No. 9, pp. 847-850.
Okamoto et al., "Evaluation of Chitin and Chitosan on Open Wound Healing in Dogs", J. Vet. Med. Sci., 1995, vol. 57, No. 5, pp. 851-854.
Written Opinion of the International Searching Authority issued in PCT/JP2014/083954 (PCT/ISA/237), dated Apr. 21, 2015.
Extended European Search Report, dated Jun. 21, 2017, for European Application No. 14874363.6.
Nascimento et al., "Evaluation of chitosan gel with 1% silver sutfadiazine as an alternative for burn wound treatment in rats," Acta Cirúrgica Brasileira, vol. 24, No. 6, Nov.-Dec. 2009, XP055380644, pp. 460-465.

* cited by examiner

GEL-FORMING AGENT COMPRISING SULFA AGENT AND CHITOSAN AGENT AND HAVING POWDERED DOSAGE FORM

TECHNICAL FIELD

The present invention relates to a gel-forming agent comprising a sulfa agent and chitosan agent and having a powdered dosage form, more particularly, to a gel-forming agent for protecting an exudative affected area, and even more particularly, to a gel-forming agent for treating a wound. In addition, the present invention provides a kit containing a gel-forming agent, a method for forming a gel at a target affected area comprising a step for applying a gel-forming agent, more particularly, a method for protecting an exudative affected area, and even more particularly, a wound treatment method.

BACKGROUND ART

Wounds observed in the clinical context impose severe physical, emotional and financial burdens on subject suffering from wounds. In animals, including humans, inadequate treatment of wounds increases the risk of bacterial infection. When a wound becomes infected by bacteria, symptoms such as abscess, cellulitis or exudate are manifest at the wound site, resulting in tissue damage and prolongation of treatment. In addition, the wound surface may become discolored and form abnormal granulation tissue, resulting in the onset of pain, reddening or a foul odor.

Sulfa agents have long been used to prevent and treat infections. Sulfa agents refer to the generic term for synthetic compounds having a sulfonamide group. Sulfa agents antagonistically inhibit para-aminobenzoic acid, the substrate of dihydropteroate synthase, which is an essential enzyme of the folic acid synthesis pathway. As a result, sulfa agents demonstrate an antibacterial action by inhibiting folic acid synthesis, as well as DNA/RNA synthesis requiring folic acid, in bacteria.

In addition, sulfa agents demonstrate a blood pH-lowering action by preventing the formation of bicarbonate ions by inhibiting carbonic anhydrase. As a result, antibacterial action is demonstrated by lowered wound pH to a pH below the optimum pH for bacterial growth.

Chitosan agents are also widely used in wound treatment. Chitosan agents having a D-glucosamine polymer as the main component thereof induce fibroblasts to promote granulation and accelerate wound healing when applied to a wound site.

A pharmaceutical cream is known for restoring skin and treating bacterial skin infections that contains a sulfa agent and chitosan agent (Patent Document 1).

PRIOR ART DOCUMENTS

Patent Documents

Patent Document 1: International Publication No. WO 2010-119369

DISCLOSURE OF THE INVENTION

Problems to be Solved by the Invention

Since sulfa agents are only slightly soluble in water and end up drying immediately, they were required to adopt the dosage form of a cream when used as a wound healing agent. However, the cream is applied by the person performing treatment while repeatedly making direct contact with the wound site, thereby subjecting to the patient to irritating pain while also requiring a technique to ensure the cream is applied uniformly.

Chitosan agents may cause excessive promotion of granulation or exacerbate inflammation by promoting bacterial growth as a result of having a somewhat high pH, thereby resulting in the problem of handling difficulties when used as a wound healing agent.

In addition, since creams facilitate the adherence of hair, clothing and dust from the outside, it is difficult to keep the wound site clean. Although adhesive sheets have been provided to improve on this problem, adhesive sheets have problems such as difficulty in sticking to joints or wound sites having a highly irregular surface or wounds covered with hair, reinjuring normal skin or granulated wound sites when peeled from the skin where the adhesive sheet is adhered, or causing the patient pain when peeled from the skin.

Means for Solving the Problems

As a result of conducting extensive studies, the inventor of the present invention found that the aforementioned problems are solved by using a composition containing a sulfa agent and a chitosan agent in a powdered dosage form, thereby leading to completion of the present invention.

Namely, the gist of the present invention is as indicated below.

[1] A gel-forming agent comprising a sulfa agent and a chitosan agent and having a powdered dosage form.

[2] The gel-forming agent described in [1] for protecting an exudative affected area.

[3] The gel-forming agent described in [1] or [2] for treating a wound.

[4] The gel-forming agent described in any of [1] to [3], wherein the sulfa agent is selected from the group consisting of sulfamonomethoxine, acetylsulfamethoxazole, salazosulfapyridine, sulfadiazine, silver sulfadiazine, sulfadimethoxine, sulfathiazole, sulfaphenazole, sulfamethoxazole, sulfamethoxypyridazine, sulfamethopyrazine, sulfamethomidine, sulfamethizole, sulfamerazine, sulfisoxazole, sulfisomidine, sulfisomidine sodium, homosulfamine and derivatives thereof.

[5] The gel-forming agent described in any of [1] to [4], wherein the sulfa agent is sulfamonomethoxine or a derivative thereof.

[6] The gel-forming agent described in any of [1] to [5], wherein the chitosan agent is a mixture of a high molecular weight chitosan and a low molecular weight chitosan.

[7] The gel-forming agent described in any of [1] to [6], wherein the chitosan agent contains chitin.

[8] The gel-forming agent described in any of [1] to [7], wherein the sulfa agent and the chitosan agent are mixed at a weight ratio of 20:1 to 1:20.

[9] The gel-forming agent described in any of [1] to [8], wherein the sulfa agent and the chitosan agent are mixed at a weight ratio of 5:1 to 1:5.

[10] The gel-forming agent described in any of [1] to [9], wherein the affected area is an acute wound selected from the group consisting of an incised wound, laceration, abrasion, puncture wound, penetrating wound, bruise, hematoma and crush wound.

[11] The gel-forming agent described in any of [1] to [9], wherein the affected area is a chronic wound selected from the group consisting of a wounds caused by venous ulcer, diabetic ulcer, decubital ulcer, corneal ulcer, digestive ulcer, ischemia, radiation injury, stomatitis and skin disease.

[12] The gel-forming agent described in any of [1] to [11], wherein the subject is a bird, reptile, amphibian, fish or mammal.

[13] The gel-forming agent described in [12], wherein the subject is a mammal selected from the group consisting of a dog, cat, horse, sheep, cow and human.

[14] A method for producing the gel-forming agent described in any of [1] to [13], comprising: a step for mixing a sulfa agent and a chitosan agent.

[15] A powdered sulfa agent for applying separately and consecutively or simultaneously in combination with a powdered chitosan agent to an affected area of a subject.

[16] A powdered chitosan agent for applying separately and consecutively or simultaneously in combination with a powdered sulfa agent to an affected area of a subject.

[17] A gel formation kit comprising the gel-forming agent described in any of [1] to [13], the sulfa agent described in [15] or the chitosan agent described in [16], and a powder dissipating container.

[18] The gel formation kit described in [17], wherein the powder dissipating container is in the shape of an dropper.

[19] A method for forming a gel at an affected area of a subject, comprising: a step a) for combining a sulfa agent and a chitosan agent, each in the form of a powder, and separately and consecutively or simultaneously applying at an affected area of a subject.

[20] The method described in [19] for protecting an exudative affected area.

[21] The method described in [19] or [20] for treating a wound.

[22] The method described in any of [19] to [21], wherein the sulfa agent is selected from the group consisting of sulfamonomethoxine, acetylsulfamethoxazole, salazosulfapyridine, sulfadiazine, silver sulfadiazine, sulfadimethoxine, sulfathiazole, sulfaphenazole, sulfamethoxazole, sulfamethoxypyridazine, sulfamethopyrazine, sulfamethomidine, sulfamethizole, sulfamerazine, sulfisoxazole, sulfisomidine, sulfisomidine sodium, homosulfamine and derivatives thereof.

[23] The method described in any of [19] to [22], wherein the sulfa agent is sulfamonomethoxine or a derivative thereof.

[24] The method described in any of [19] to [23], wherein the chitosan agent is a mixture of a high molecular weight chitosan and a low molecular weight chitosan.

[25] The method described in any of [19] to [24], wherein the chitosan agent comprises chitin.

[26] The method described in any of [19] to [25], wherein the applied sulfa agent and chitosan agent are mixed at a weight ratio of 20:1 to 1:20.

[27] The method described in any of [19] to [26], wherein the applied sulfa agent and chitosan agent are mixed at a weight ratio of 5:1 to 1:5.

[28] The method described in any of [19] to [27], wherein the applied sulfa agent and chitosan agent are mixed in advance.

[29] The method described in any of [19] to [28], wherein the application consists of applying directly to an affected area.

[30] The method described in any of [19] to [29], wherein the application uses a dissipating container.

[31] The method described in any of [19] to [30], wherein the affected area is an acute wound selected from the group consisting of an incised wound, laceration, abrasion, puncture wound, penetrating wound, bruise, hematoma and crush wound.

[32] The method described in any of [19] to [30], wherein the affected area is a chronic wound selected from the group consisting of a wounds caused by venous ulcer, diabetic ulcer, decubital ulcer, corneal ulcer, digestive ulcer, ischemia, radiation injury, stomatitis and skin disease.

[33] The method described in any of [19] to [32], wherein the subject is a bird, reptile, amphibian, fish or mammal.

[34] The method described in [33], wherein the subject is a mammal selected from the group consisting of a dog, cat, horse, sheep, cow and human.

Effects of the Invention

According to the present invention, a wound healing composition is provided that has a wound healing effect that is more remarkable than that of a conventional sulfa agent or chitosan agent alone. Namely, a powder containing a sulfa agent and a chitosan agent maintains the pH of a wound site within a range at which greater healing effects are demonstrated and exhibits antibacterial action of a sulfa agent. The wound site is kept at suitable moist condition to form granulation appropriately. In addition, as a result of having a powder for the dosage form, the use of a suitable dissipating container makes it possible to disperse the wound healing composition without the person performing treatment making direct contact with the wound site. Moreover, a gel layer is surprisingly formed by interaction between the sulfa agent and the chitosan agent when the powder contacts body fluid at the wound site, thereby also fulfilling the role of protecting the wound site.

BEST MODE FOR CARRYING OUT THE INVENTION

Figure 1:
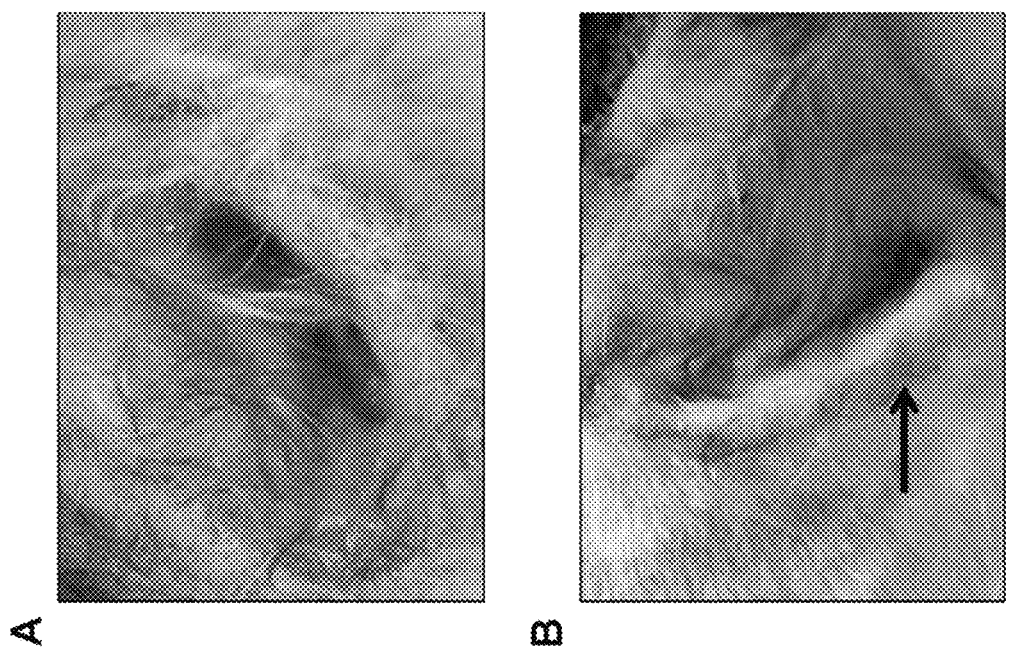
FIG. 1 shows the formation of a gel layer at a wound site by the gel-forming agent of the present invention.

The present invention provides a gel-forming agent comprising a sulfa agent and a chitosan agent and having a powdered dosage form, more particularly, a gel-forming agent for protecting an exudative affected area, and even more particularly, a gel-forming agent for treating a wound.

The gel-forming agent of the present invention comprises a sulfa agent. In the present invention, the sulfa agent refers to an arbitrary synthetic compound having a sulfonamide group that can be presumed to be used in a pharmaceutical. Specific examples thereof include, but are not limited to, sulfamonomethoxine, acetylsulfamethoxazole, salazosulfapyridine, sulfadiazine, silver sulfadiazine, sulfadimethoxine, sulfathiazole, sulfaphenazole, sulfamethoxazole, sulfamethoxypyridazine, sulfamethopyrazine, sulfamethomidine, sulfamethizole, sulfamerazine, sulfisoxazole, sulfisomidine, sulfisomidine sodium and homosulfamine. These sulfa agents may also be in the form of a derivative or a salt such as a silver salt. In a certain specific mode, the sulfa agent is sulfamonomethoxine or a sulfadimethoxine. In addition, in a different mode, the sulfa agent is sulfamonomethoxine.

The gel-forming agent of the present invention comprises a chitosan agent. In the present invention, a chitosan agent refers to a mixture having a linear polymer of D-glucosamine in the form of chitosan as the main component thereof. There are no particular limitations on the degree of polymerization or molecular weight of the chitosan agent. In a certain specific mode, the chitosan agent of the present invention is a mixture of a high molecular weight chitosan (molecular weight: 10,000 or more) and a low molecular weight chitosan (molecular weight: less than 10,000). Although there are no particular limitations on the mixing ratio of the high molecular weight chitosan and low molecular weight chitosan, an example thereof is a mixing ratio having a weight ratio of 1:9 to 9:1.

The chitosan agent in the present invention may further contain chitin. Chitin refers to a linear polymer of N-acetyl glucosamine and glucosamine. There are no particular limitations on the degree of polymerization of the chitin, and may be an oligosaccharide (degree of polymerization: 3 to 10). In the case chitin is contained in the chitosan agent of the present invention, the content of chitin is preferably a weight ratio of 15% or less.

In a preferable mode thereof, the gel-forming agent of the present invention comprises sulfamonomethoxine and a chitosan agent comprising chitin. In a more preferable mode, the ratio of high molecular weight chitosan to low molecular weight chitosan to chitin oligosaccharide in the chitosan agent comprising chitin is a weight ratio of 39:59:2.

In the gel-forming agent of the present invention, there are no particular limitations on the mixing ratio of the sulfa agent and chitosan agent of the present invention, and can be set as desired corresponding to the type and severity of the wound. In a certain mode, the sulfa agent and chitosan agent of the present invention are mixed at a weight ratio of 20:1 to 1:20. In a preferable mode, the sulfa agent and the chitosan agent are mixed at a weight ratio of 5:1 to 1:5. It is preferable to increase the mixing ratio of the sulfa agent in the case of a high degree of bleeding, exudation or serious infection is observed at the wound site or in the case of advanced granulation, and for example, the gel-forming agent of the present invention in which the sulfa agent and chitosan agent are mixed at a weight ratio of 21:5 is preferable. In the case of containing an excipient in this mode, the sulfa agent, chitosan agent and excipient are mixed at a weight ratio of, for example, 21:5:84. On the other hand, it is preferable to lower the mixing ratio of the sulfa agent in the case serious damage is observed at the wound site or prior to granulation, and for example, the gel-forming agent of the present invention in which the sulfa agent and chitosan agent are mixed at a weight ratio of 7:15 is preferable. In this case of containing an excipient in this mode, the sulfa agent, chitosan agent and excipient are mixed at a weight ratio of, for example, 7:15:28.

The dosage form of the gel-forming agent of the present invention is a powder. A powder refers to a powdered dosage form. Although there are no particular limitations on the particle diameter of the powder, it is preferably a particle diameter that allows the powder to pass through a sieve having an opening size of 500 μm. A powder of this particle size enables the gel-forming agent of the present invention to be applied uniformly without the person performing treatment making direct contact with the affected area by using, for example, a dissipating container. There are no particular limitations on the method used to formulate the gel-forming agent of the present invention into the dosage form of a powder provided it is a method commonly carried out for pharmaceutical preparations, and may be granulation in order to demonstrate the effects of the present invention. Examples of granulation methods include disintegrating granulation, extrusion granulation, fluidized-bed granulation, spray granulation, tumbling granulation and agitation granulation.

As a result of the gel-forming agent of the present invention having a powdered dosage form, a drug can be applied without limiting the location, form or state of the affected area.

Moreover, as a result of the gel-forming agent of the present invention having a powdered dosage form, the sulfa agent and chitosan agent interact with moisture resulting in the formation of a somewhat gel-like layer when the drug is applied to an exudative affected area and contacts a body fluid such as blood, saliva or exudate. In this manner, as a result of a gel layer being formed at an exudative affected area, the gel-forming agent is easily retained at the wound site while also simultaneously fulfilling the role of a protective sheet. The surface of the sheet has low viscosity and prevents foreign objects from adhering to the wound site.

The thickness and degree of solidity of the gel layer formed by the gel-forming agent of the present invention as described above is adjusted spontaneously according to the degree of severity of the affected area. Namely, in the case a wound is severe and there is a large amount of exudate, the gel-forming agent of the present invention adheres in a thick layer, while in the case the wound is healing and there is little exudate, the gel-forming agent of the present invention adheres in a thin layer. In addition, unnecessary powder comes off spontaneously accompanying body movement. Furthermore, the gel layer can be easily removed with water or physiological saline without causing intense pain or injury to the patient.

The gel-forming agent of the present invention may also contain an arbitrary pharmacologically acceptable excipient, vehicle or diluent provided the effects of the present invention are not lost. Specific examples of excipients include, but are not limited to, lactose, sucrose and cornstarch.

The gel-forming agent of the present invention can be used at an arbitrary affected area. The affected area may be a skin surface, mucous membrane, oral cavity, digestive organ or urinary bladder. Specific examples of wounds include acute wounds selected from the group consisting of an incised wound, laceration, abrasion, puncture wound, penetrating wound, bruise, hematoma and crush wound, and chronic wounds selected from the group consisting of venous ulcer, diabetic ulcer, decubital ulcer, corneal ulcer, digestive ulcer, ischemia, radiation injury, stomatitis and skin disease.

A subject to which the gel-forming agent of the present invention is applied is an arbitrary animal that has incurred a wound. Examples of subjects include, but are not limited to, birds, reptiles, amphibians, fish and mammals. In a certain mode, the subject is a mammal, and examples thereof include a dog, cat, horse, sheep, cow and human.

There are no particular limitations on the method used to apply the gel-forming agent of the present invention to an affected area provided the dosage form of the gel-forming agent of the present invention is a powder. In a certain mode, the gel-forming agent of the present invention is applied without the person performing treatment making direct contact with the wound site by using a powder dissipating container. The dissipating container used in this case may be an arbitrary container capable of dispersing the gel-forming agent of the present invention, and an eyedropper, for example, may be used to apply the gel-forming agent of the present invention.

The present invention also provides a method for producing the gel-forming agent of the present invention that comprises mixing a sulfa agent, a chitosan agent, and an excipient as necessary.

Examples of raw materials preferably used in the production method of the present invention include each of the compounds exemplified in the gel-forming agent of the present invention.

There are no particular limitations on the method used to acquire each of the raw materials used in the production method of the present invention. The chitosan agent may be obtained by deacetylation of chitin using a known method.

There are no particular limitations on the mixing method used in the production method of the present invention provided the sulfa agent and the chitosan agent are uniformly mixed in the form of a powder. In a certain mode, a chitosan agent having a low specific gravity is first placed in a mixing container followed by the addition of a sulfa agent having a high specific gravity and mixing by stirring. According to this mode, the raw materials are mixed more rapidly and uniformly.

The present invention also provides a powdered sulfa agent for applying to an affected area of a subject either separately and consecutively or simultaneously by combining with a powdered chitosan agent in order to form a gel, more particularly, to protect an exudative affected area, and even more particularly, to treat a wound.

Specific examples of the powdered sulfa agent of the present invention include sulfa agents exemplified in the gel-forming agent of the present invention.

The present invention also provides a powdered chitosan agent for applying to an affected area of a subject either separately and consecutively or simultaneously by combining with a powdered sulfa agent in order to form a gel, more particularly, to protect an exudative affected area, and even more particularly, to treat a wound.

Specific examples of the powdered chitosan agent of the present invention include chitosan agents exemplified in the gel-forming agent of the present invention.

In addition, the present invention provides a gel formation kit containing the gel-forming agent of the present invention, a powdered sulfa agent for applying by combining with a chitosan agent or a powdered chitosan agent for applying by combining with a sulfa agent, and depending on the case, a dissipating container.

In a certain mode, the gel formation kit of the present invention contains a powder dissipating container. The powder dissipating container is an arbitrary container capable of dispersing the gel-forming agent of the present invention, and is an eyedropper container, for example.

Preferable examples of the sulfa agent and chitosan agent in the gel formation kit of the present invention include each of the compounds exemplified in the gel-forming agent of the present invention.

The present invention provides a method for forming a gel at an affected area of a subject, more particularly, a method for protecting an exudative affected area, and even more particularly, a method for treating a wound, comprising:

a step a) for combining a sulfa agent and a chitosan agent, each in the form of a powder, and separately and consecutively or simultaneously applying at an affected area of a subject.

According to this method, wounds that were unable to be adequately healed using a conventional treatment method can be healed to a degree that they do not have an effect on the daily life of the subject.

In the method of the present invention, the sulfa agent and the chitosan agent may be applied separately and consecutively, or may be applied simultaneously. In the case of applying simultaneously, they can be preferably applied as a mixture of the two.

Examples of the powdered sulfa agent and chitosan agent applied in the method of the present invention include each of the compounds exemplified in the gel-forming agent of the present invention.

In a certain mode of the method of the present invention, the powder is directly applied to an affected area, and more particularly, to an exudative affected area or wound site. Applying directly refers to applying the powder as is.

In a certain mode of the method of the present invention, a dissipating container can be used during application. The dissipating container is an arbitrary container capable of spraying the gel-forming agent of the present invention, and is, for example, an eyedropper container.

In a certain mode thereof, the method of the present invention further comprises a step for preliminarily rinsing the affected area with water, physiological saline, or water or physiological saline containing a sulfa agent prior to applying the sulfa agent and chitosan agent to the affected area. An example of the water containing the sulfa agent is an aqueous solution of sulfamonomethoxine having a concentration of 0.02% (w/v).

A wound in the method of the present invention is a wound to which the gel-forming agent of the present invention can be applied.

The subject in the method of the present invention is a subject to which the gel-forming agent of the present invention can be applied, and is an arbitrary animal, and preferably a mammal.

There are no particular limitations on the applied amounts of the sulfa agent and chitosan agent in the method of the present invention provided the effects of the present invention are demonstrated. The applied amounts are sufficient for enabling the gel-forming agent of the present invention to cover an affected area. Since the gel-forming agent of the present invention is a powder, even if applied to the affected area in excess, the excess amount comes off as previously described. In a certain mode, the sulfa agent and chitosan agent of the present invention can each be retained at the affected area at 1 μg to 30 mg per 1 cm$^2$.

There are no particular limitations on the number and frequency of applications of the method of the present invention provided the effects of the present invention are demonstrated. In a certain mode, the application frequency is 1, 2, 3, 4 or 5 times per day, once every 2 days, once every 3 days, once every 4 days, once every 5 days, once every 6 days or once a week.

EXAMPLES

Although the following provides a more detailed explanation of the present invention through examples thereof, the present invention is not limited to the following examples provided the gist thereof is not exceeded.

[Preparation of Drug Combination Powder Containing Sulfa Agent and Chitosan Agent]

20% Daimeton Powder (Meiji Seika Pharma Co., Ltd.) was used for the sulfa agent. Daimeton Powder is a powder containing 20 g of sulfamonomethoxine in 100 g thereof.

A powder obtained by mixing a high molecular weight chitosan (Flonac H, Nippon Suisan Kaisha, Ltd.), a low molecular weight chitosan (Flonac C-100M, Nippon Suisan Kaisha, Ltd.), and a chitin oligosaccharide at a respective weight ratio of 39:59:2 was used for the chitosan agent (Morikensho Co, Ltd., Japan). Furthermore, the degrees of purification (degrees of deacetylation) of the high molecular weight chitosan and low molecular weight chitosan were both about 90%, and are thought to contain about 10% non-deacetylated chitin.

Drug combination powders containing the sulfa agent and chitosan agent were prepared in the manner indicated below.

| Drug Combination Powder 1 | |
|---|---|
| Volume ratio: 1:1 | Volume: 10 ml |
| Daimeton Powder | 3.5 g (0.7 g sulfamonomethoxine) |
| Chitosan agent | 1.5 g |
| Drug Combination Powder 2 | |
| Volume ratio: 9:1 | Volume: 10 ml |
| Daimeton Powder | 6.3 g (1.26 g sulfamonomethoxine) |
| Chitosan agent | 0.3 g |

Each of the drug combination powders was filled into a 10 ml eye drop bottle in the order of the chitosan agent followed by the sulfa agent and then mixed by shaking well.

[Method Used to Disperse Drug Combination Powders onto Wound Sites]

In the following examples, drug combination powders were dispersed onto wound sites in the manner indicated below as a general rule.

(1) The area around the wound site was shaved.

(2) The wound site was washed with 0.1% Daimeton suspension (in water).

(3) Drug Combination Powder 1 or Drug Combination Powder 2 was dispersed in a thin layer onto the wound site until the wound site and the area around the wound site became white.

(4) The treatment of steps (2) and (3) was repeated once a day.

Typically, as shown in FIG. 1, the formation of a gel-like layer is observed following treatment with a drug combination powder. Although drainage and discharge of exudate from the wound site were observed prior to treatment with the drug combination powder (FIG. 1A), the drug combination powder was observed to absorb the exudate, gel, and form a layer following treatment (arrow in FIG. 1B).

[pH Measurement]

In the following examples, changes in pH were measured using the SkinCheck Skin pH Tester (HI 98109, Hanna Instruments Inc., U.S.A.). After wetting the flat sensor of the tester with pure water, pH was measured by contacting the flat sensor directly with the site desired to be measured.

Figure 2:
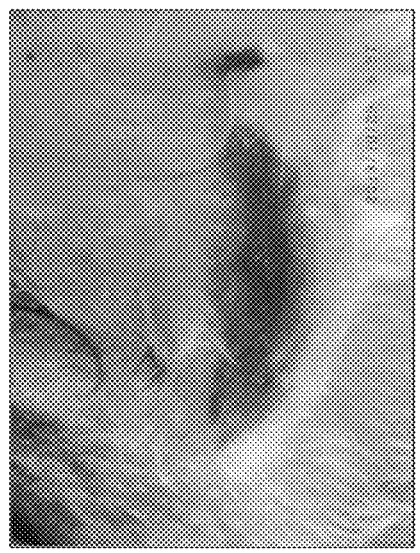
FIG. 2 shows the progress of a wound site of a Case 1 following application of the gel-forming agent of the present invention.
Figure 2:
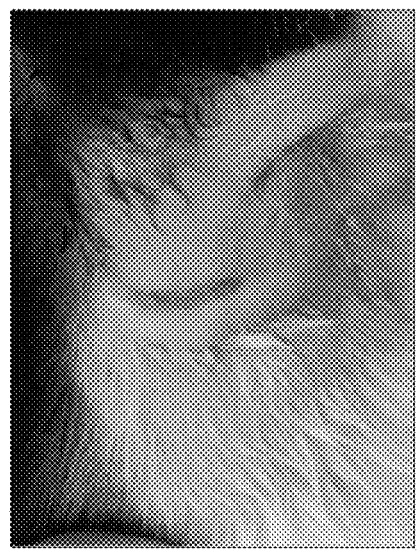
Figure 2:
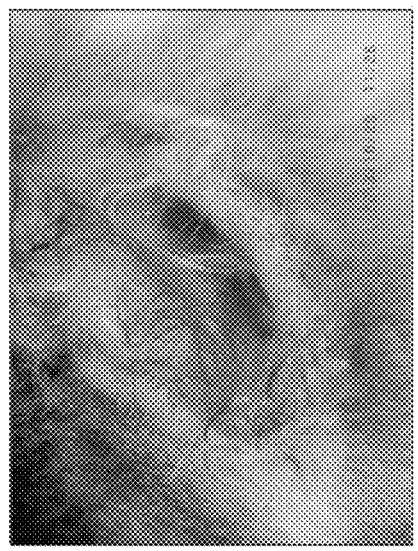
Figure 2:

Treatment Example 1: Treatment of Bite Wound in Cat with Drug Combination Powder A neutered female cat approximately 3 years old having a bite wound on the lower right side of the body was treated with Drug Combination Powder 1 (FIG. 2). Drainage was observed at the time of an initial examination performed one week after incurring the injury and the diameter of missing epithelium was 3.3 cm (FIG. 2A). When Drug Combination Powder 1 was dispersed onto the wound site in accordance with the previously described procedure, drainage had already stopped one day after the start of treatment and granulation was observed over the entire wound site (FIG. 2B). When the wound site was subsequently continued to be treated daily with Drug Combination Powder 1, the size of the wound site decreased and epithelialization was observed 4 days after the start of treatment (FIG. 2C), and epithelium covered the entire wound site and the damaged skin was favorably regenerated 6 days after the start of treatment (FIG. 2D). When changes in pH at the wound site were measured during the course of treatment, the pH was found to range between pH 5 and pH 7. In addition, although slight pain was observed until the epithelium formed when the wound site was washed during treatment, the cat did not exhibit signs of pain during dispersal of the drug combination powder.

Figure 3:
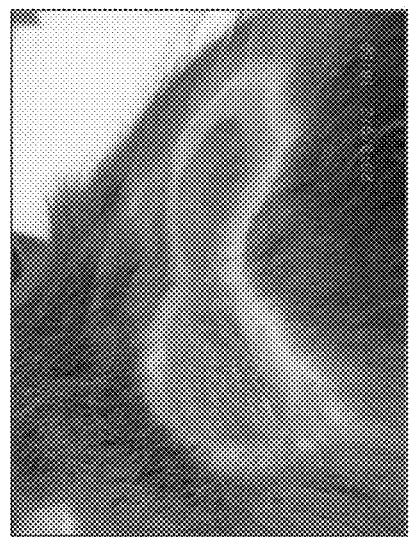
FIG. 3 shows the progress of a wound site of a Case 2 following application of the gel-forming agent of the present invention.
Figure 3:
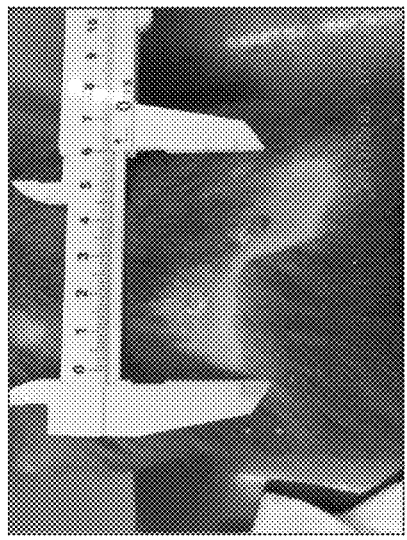
Figure 3:
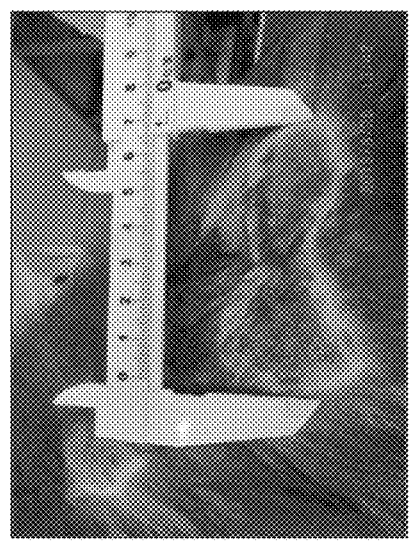
Figure 3:
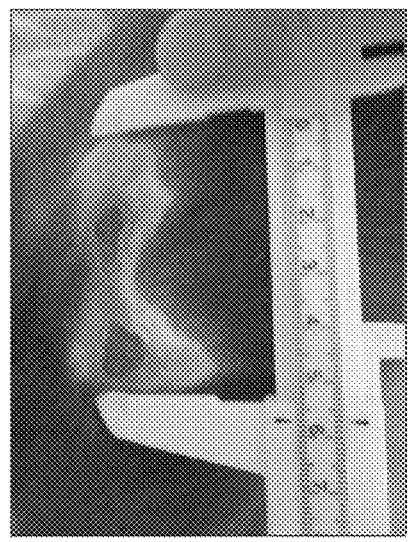

Treatment Example 2: Treatment of Skin Burn Wound in Dog with Drug Combination Powder A six-year-old male dog that had been burned on the back by deep frying oil was treated with Drug Combination Powder 1. Although Daimeton Powder had been applied to the wound site at home for 23 days starting immediately after the injury, the diameter of missing epithelium remained at 7 cm without exhibiting improvement, and pain, bleeding and exudate discharge were also observed (FIG. 3A). Thus, when the wound was treated once a day with Drug Combination Powder 1 in accordance with the previously described procedure (accompanied simultaneously by oral administration of an antibiotic (cephalexin) for the first 5 days only), pain, bleeding and exudate discharge were no longer observed 8 days after the start of treatment, and granulation was observed over the entire area of missing epithelium (FIG. 3B). When treatment was subsequently continued, the size of the wound site decreased in size 18 days after the start of treatment (FIG. 3C). Formation of epithelium was observed over the entire wound site 26 days after the start of treatment. Although slight pain was observed until the epithelium formed when the wound site was washed during treatment, the dog did not exhibit signs of pain during dispersal of the drug combination powder.

Figure 4:
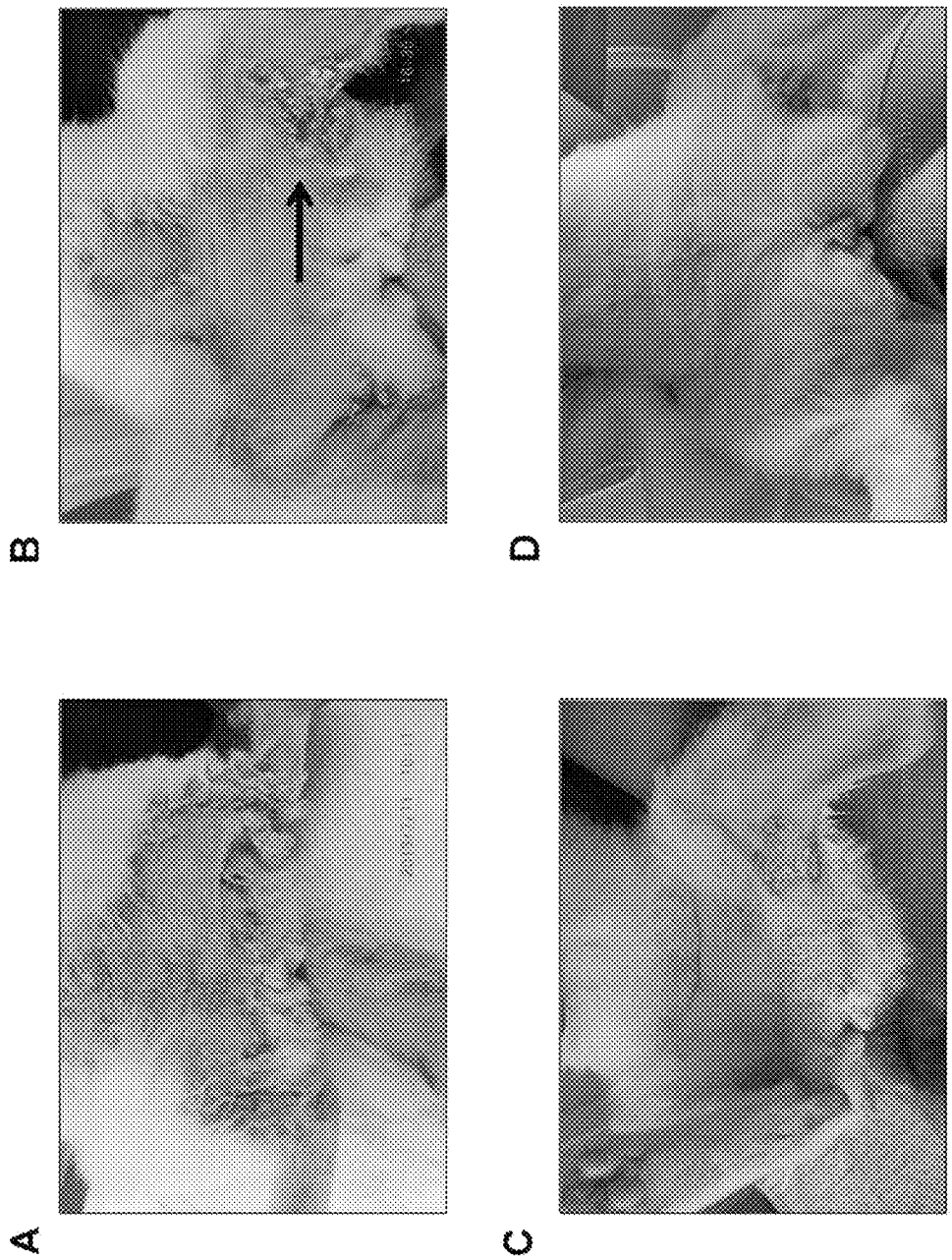
FIG. 4 shows the progress of a wound site of a Case 3 following application of the gel-forming agent of the present invention.

Treatment Example 3: Treatment of Skin Burn Wound in Cat with Drug Combination Powder An 8-month-old female cat that had been burned on the thighs with hot water was treated with Drug Combination Powder 2. Pain, heat sensation and exudate discharge were observed at the time of the injury, and redness and hair loss were observed at the wound site. When the wound site was washed and treated by dispersing Drug Combination Powder 2 (while simultaneously treating by intravenous infusion and antibiotic) at the wound site during hospitalization for 8 days starting immediately after the injury, although exudate discharge was still observed, regeneration of epithelium was observed over the entire wound site (FIG. 4A). Since the wound site was observed to have improved, when the cat was discharged and status was monitored at home after switching treatment to Daimeton Powder administered once a day, epithelialization did not progress on the left inner thigh only and exudate discharge was still observed even after 11 days had passed since switching treatment (19 days after injury) (arrow in FIG. 4B). Although treatment with Daimeton was continued until about 1 month had elapsed following injury, epithelialization of the left inner thigh was still not observed and improvement was also not observed (FIG. 4C). Therefore, when treatment with Drug Combination Powder 2 was started about 2 months after the injury, improvement was observed immediately, and when the cat was monitored for 1 month after the start of treatment with Drug Combination Powder 2 (about 3 months after injury), the left inner thigh had epithelialized completely (FIG. 4D). Although slight pain was observed until the epithelium formed when the wound site was washed during treatment, the cat did not exhibit signs of pain during dispersal of the drug combination powder.

Figure 5:
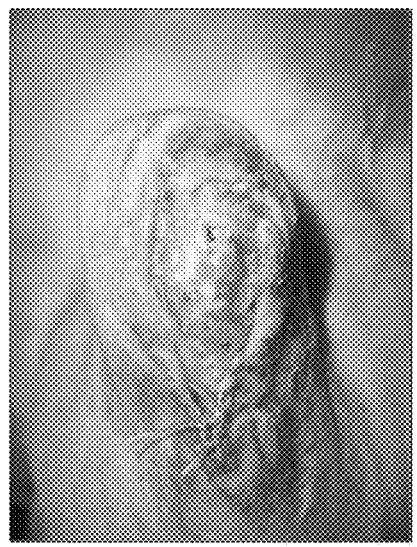
FIG. 5 shows the progress of a wound site of a Case 4 following application of the gel-forming agent of the present invention.
Figure 5:
Figure 5:
Figure 5:
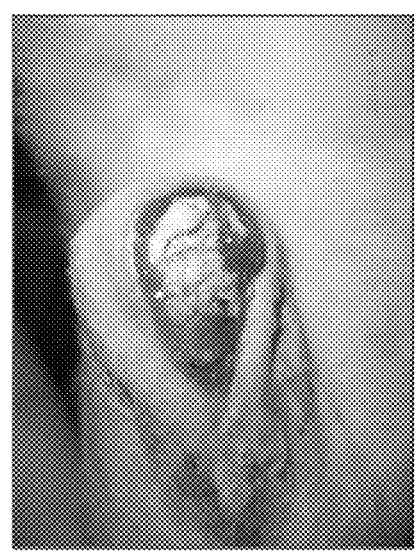

Treatment Example 4: Treatment of Sutured Site Following Amputation in Cat with Drug Combination Powder A male cat approximately one year old underwent amputation after having incurred a carpal fracture caused by a steel trap. Although amputation at the scapular joint would normally be performed since the wound site exhibited necrosis over a wide range several days after the injury, the leg was amputated at the left elbow joint in order to preserve the possibility of being able to walk smoothly without assistance followed by suturing of the amputated site. Five days after surgery (FIG. 5A), since the sutured site had opened up exposing the sutured muscle tissue (FIG. 5B), it was thought to be necessary to repeat amputation at the scapular joint. However, status improved following treatment of the sutured site with Drug Combination Powder 1 in accordance with the previously described procedure (while simultaneously administering antibiotic (sawacillin)). Granulation was observed over the entire originally sutured site and epithelialization was observed around the originally sutured site 8 days after the start of treatment with Drug Combination Powder 1 (13 days after amputation) (FIG. 5C). The wound site was present only on the end of the amputated leg and regeneration of skin was observed 16 days after the start of treatment with Drug Combination Powder 1 (21 days after amputation) (FIG. 5D). Status of the wound subsequently progressed favorably and the cat recovered to the extent that he was able to run around outside. In addition, although slight pain was observed until the epithelium formed when the wound site was washed during treatment, the cat did not exhibit signs of pain during dispersal of the drug combination powder.

Treatment Example 5: Treatment of Decubitus in a Cat Hind Legs with a Drug Combination Powder Using Sulfadimethoxine An approximately 13-year-old cat with decubitus in both hind legs was treated with a Drug Combination Powder 3 having the same composition as Drug Combination Powder 2 with the exception of using sulfadimethoxine (Abcid (Powder), Daiichi Sankyo Co., Ltd., Japan) instead of sulfamonomethoxine. Since the cat was suffering from feline immunodeficiency disease causing skin over the entire body to be thin and be easily damaged as a result of contacting the floor, status was maintained by dispersing Abcid powder at those sites of the hind legs that contacted the floor and then wrapping with tape. However, as general condition worsened, the areas of missing skin where the hind limbs contacted the floor increased in size, eventually leading to missing epithelium over a diameter of 1.5 cm, bleeding and ulceration. Thus, when the affected areas were treated with Drug Combination Powder 3 once a day in accordance with the previously described procedure followed by taping, bleeding was no longer observed, ulceration improved, and a film had formed over the area of missing skin on the following day. Similar treatment was subsequently performed every few days, and status was maintained without any exacerbation for six months until the cat died of prolonged illness. When the tape was removed while rinsing with a 0.1% suspension of Abcid during the course of treatment, the cat did not exhibit any signs of intense pain. In addition, the cat did not exhibit signs of pain during dispersal of the drug combination powder.

[Gel Layer Formation Effect of Drug Combination Powder on Blood]

A study was conducted on changes in a sulfa agent, chitosan agent and Drug Combination Powder 1 following contact with body fluid. 10 ml of physiological saline were dropped onto a double-layered non-woven gauze fabric (15 cm×15 cm) to impregnate the entire gauze fabric with the physiological saline. Subsequently, 0.5 ml of feline blood were dropped onto the gauze to a diameter of about 5 cm. Pattern paper obtained by poking out a hole having a diameter of about 4 cm in a piece of powdered paper was then prepared. The pattern paper was placed on the gauze so that the hole was positioned in the center of the circle formed by dropping the feline blood onto the gauze. Daimeton Powder, chitosan agent and Drug Combination Powder 1 were respectively dispersed in the hole by using an eyedropper. The properties of each drug that contacted the feline blood as a result of the above procedure were observed 2 hours after dispersal.

As a result, the Daimeton Powder remained on the surface of the gauze in the state of a powder 2 hours later (FIG. 6A), and a large amount of the powder came off the gauze when the gauze was tilted on an angle to remove the powder.

On the other hand, although the chitosan agent dissolved in the feline blood simultaneous to dispersal and gelled 2 hours later (FIG. 6B), the gel was quite soft, became deformed when the gauze was pressed with a finger, and took on viscosity.

Figure 6:
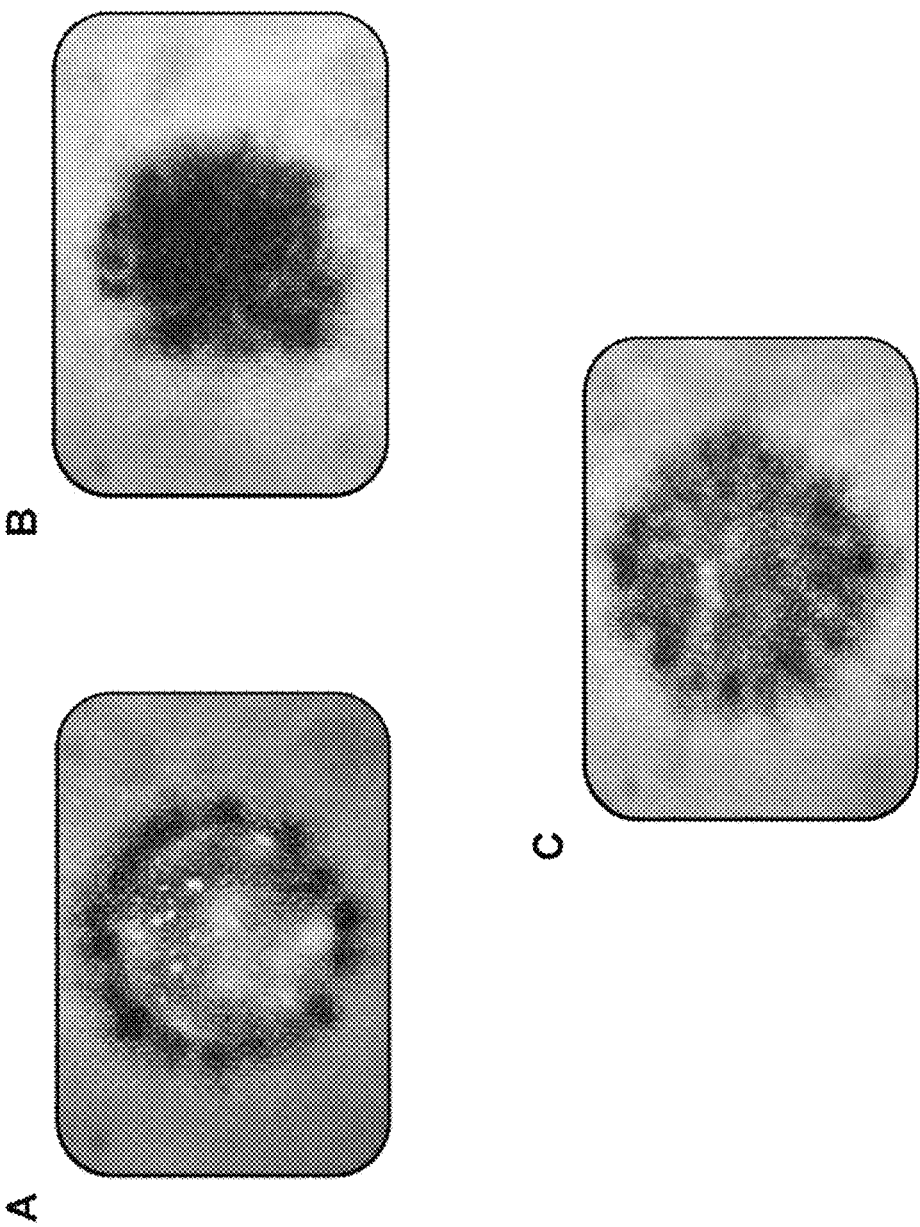
FIG. 6 shows the ability of the gel-forming agent of the present invention to form a gel layer in blood.

On the other hand, Drug Combination Powder 1 was tinted white and formed a somewhat gel-like layer (FIG. 6C). This layer had a certain degree of hardness, did not come off easily even if the gauze was tilted at an angle to remove the powder, and demonstrated little deformation even if pressed with a finger. In addition, the texture was somewhat dry.

The ability of the drug combination powder to form a gel layer as described above is thought to enable the drug combination powder to be suitably retained at the affected area while simultaneously demonstrating a protective function and a therapeutic effect over a long period of time. Furthermore, the drug combination powder is easily removed by washing with water or physiological saline.

[Measurement of Changes in pH Attributable to Drug Combination Powder]

Figure 7A:
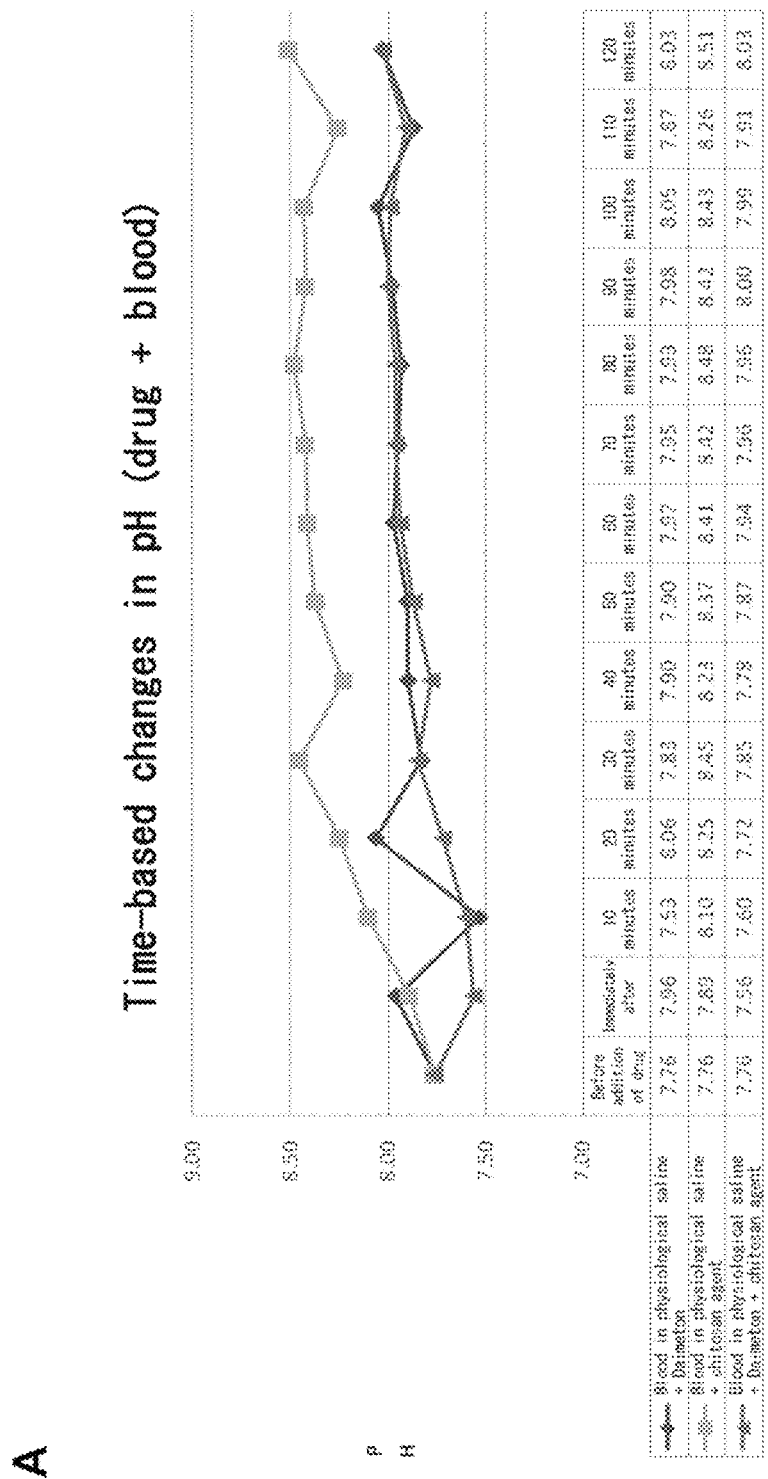
FIG. 7A shows time-based changes in pH following application of the gel-forming agent of the present invention.
Figure 7B:
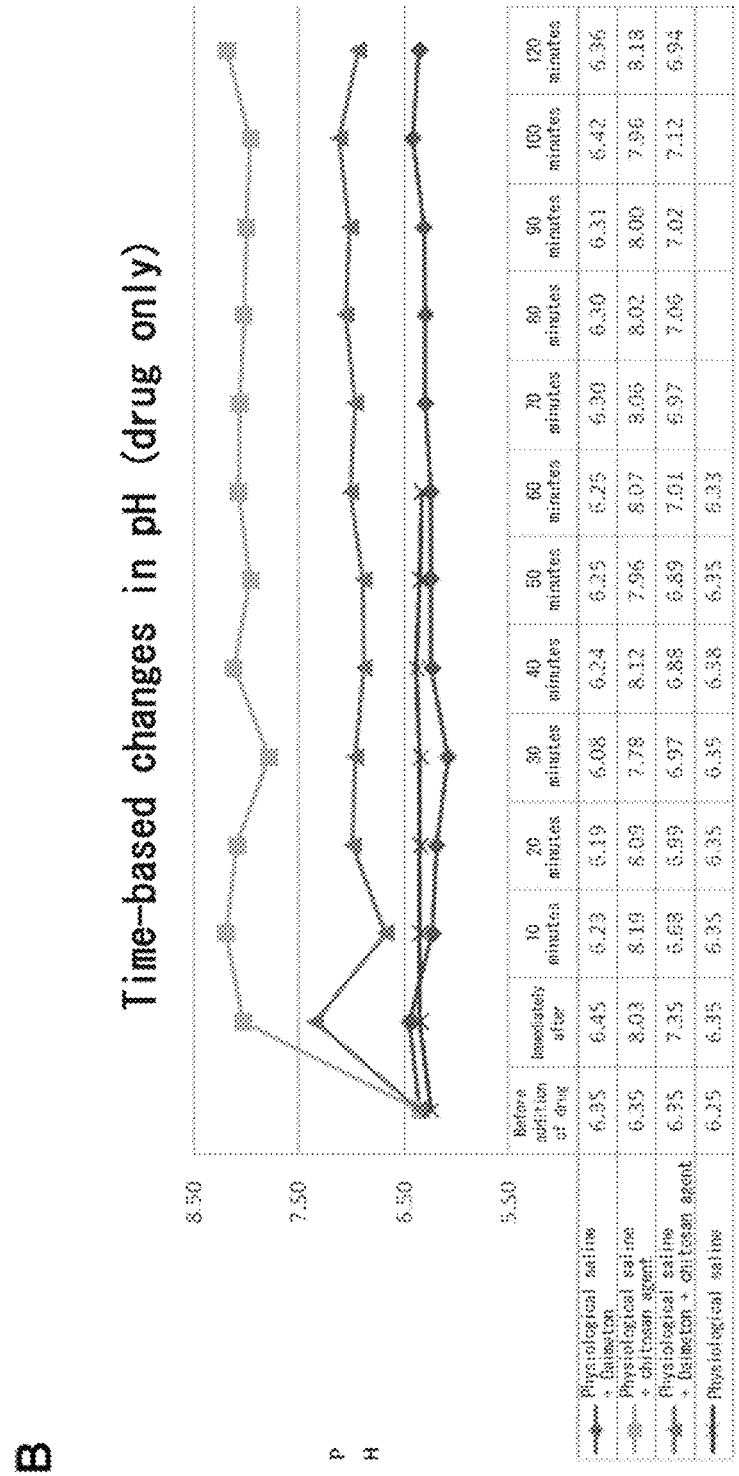
FIG. 7B shows time-based changes in pH following application of the gel-forming agent of the present invention.

A study was conducted on changes in a sulfa agent, chitosan agent and Drug Combination Powder 1 following contact with body fluid. 10 ml of physiological saline were dropped onto a double-layered non-woven gauze fabric (15 cm×15 cm) to impregnate the entire gauze fabric with the physiological saline. Subsequently, 0.5 ml of feline blood were dropped onto the gauze to a diameter of about 5 cm. Pattern paper obtained by poking out a hole having a diameter of about 4 cm in a piece of powdered paper was then prepared. The pattern paper was placed on the gauze so that the hole was positioned in the center of the circle formed by dropping the feline blood onto the gauze. Daimeton Powder (♦), chitosan agent (■) and Drug Combination Powder 1 (▲) were respectively dispersed in the hole by using an eyedropper. Time-based changes in pH at the center of each piece of gauze were then observed (FIG. 7A). Time-based changes in pH in the case of only dispersing a drug without dropping feline blood onto the gauze under the aforementioned conditions were observed as a control (FIG. 7B). At that time, pH in the case of physiological saline (X) only was also measured.

As a result, in the case of dispersing each of the drugs onto the feline blood, pH reached equilibrium at 8.0 in the case of dispersing Daimeton Powder. On the other hand, pH rose to the vicinity of 8.5 in the case of dispersing the chitosan agent. However, in the case of dispersing the drug combination powder, pH reached equilibrium at 8.0 in the same manner as in the case of the Daimeton Powder. In the case of dispersing the drug combination powder on physiological saline, although pH was lower than in the case of the chitosan agent alone, equilibrium was reached at a higher pH value than in the case of dispersing Daimeton Powder (FIG. 7B).

The aforementioned result, in which the pH value resulting from dispersal of the drug combination powder in blood is nearly the same as the pH value resulting from dispersal of the sulfa agent, suggests that, as a result of using the sulfa agent in the form of a drug combination powder, the pH lowering action attributable to a reaction between the sulfa agent and blood suppresses a bad effect by the rise in pH attributable to the chitosan agent. This ability of the drug combination powder to control pH is thought to promote wound healing effects.

Figure 8:
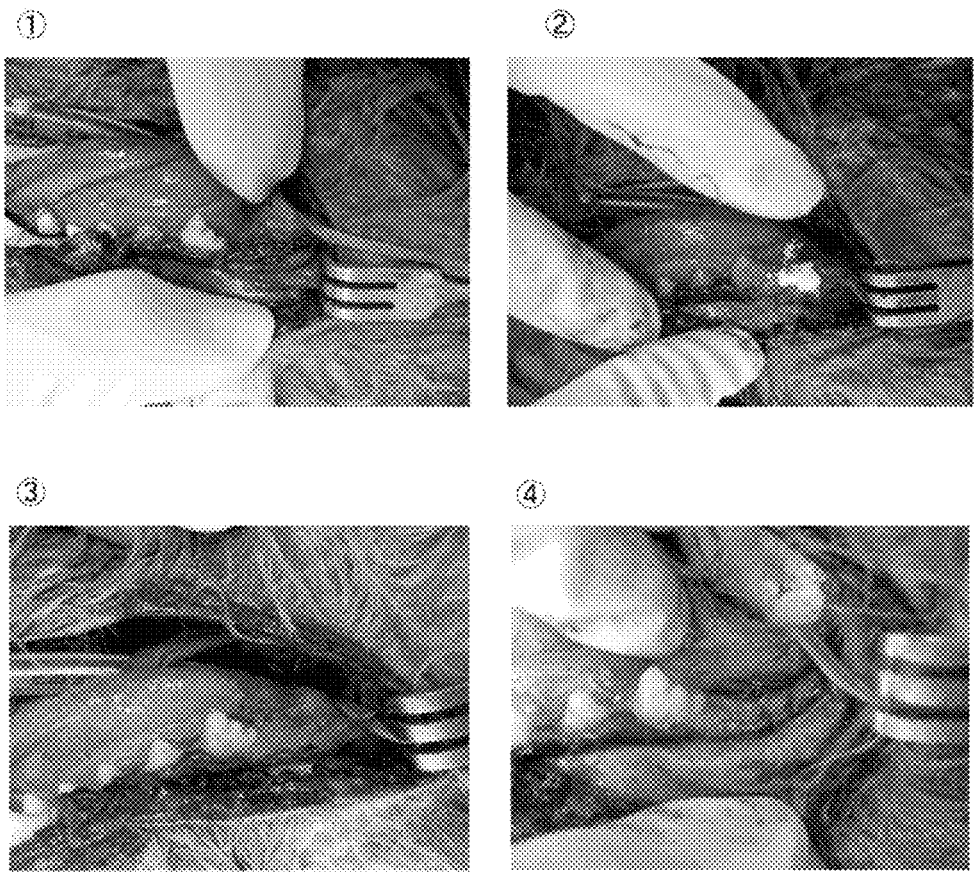
FIG. 8 shows the hemostatic and protective effects of the gel-forming agent of the present invention at a tooth extraction site in a dog.

Treatment Example 6: Hemostasis at Tooth Extraction Site in Dog by Drug Combination Powder The aforementioned Drug Combination Powder 1 was dispersed at a tooth extraction site in a dog. Hemostatic effects were demonstrated at the extraction site and gelation commenced immediately after dispersal, and protective effects were obtained 5 minutes later accompanying the suitable formation of a gel-like protective layer. The results are shown in FIG. 8.

The invention claimed is:

1. A method for treating a wound of a subject, said method comprising:
applying a sulfa agent and a chitosan agent, each in the form of a powder, to a wound site separately, consecutively, or simultaneously, whereby said sulfa agent and chitosan interact with moisture present in the wound to form a gel layer, wherein said sulfa agent is sulfamonomethoxine, wherein the pH at the wound site is maintained within the range between 5 and 7.

2. The method according to claim 1, wherein the chitosan agent is a mixture of a high molecular weight chitosan and a low molecular weight chitosan.

3. The method according to claim 1, wherein the chitosan agent contains chitin.

4. The method according to claim 1, wherein the applied sulfa agent and chitosan agent are mixed at a weight ratio of 20:1 to 1:20.

5. The method according to claim 1, wherein the applied sulfa agent and chitosan agent are mixed at a weight ratio of 5:1 to 1:5.

6. The method according to claim 1, wherein the applied sulfa agent and chitosan agent are mixed in advance.

7. The method according to claim 1, wherein the application consists of applying directly to an affected area.

8. The method according to claim 1, wherein the application uses a dissipating container.

9. The method according to claim 1, wherein the affected area is an acute wound selected from the group consisting of an incised wound, laceration, abrasion, puncture wound, penetrating wound, bruise, hematoma and crush wound.

10. The method according to claim 1, wherein the affected area is a chronic wound selected from the group consisting of a wound caused by venous ulcer, diabetic ulcer, decubital ulcer, corneal ulcer, digestive ulcer, ischemia, radiation injury, stomatitis and skin disease.

11. The method according to claim 1, wherein the subject is a bird, reptile, amphibian, fish or mammal.

12. The method according to claim 11, wherein the subject is a mammal selected from the group consisting of a dog, cat, horse, sheep, cow and human.

* * * * *